(12) United States Patent
Lo (10) Patent No.: US 9,968,477 B2
(45) Date of Patent: May 15, 2018

(54) ARM IMMOBILIZATION DEVICE AND ASSOCIATED METHODS

(71) Applicant: Ian K. Y. Lo, Calgary (CA)

(72) Inventor: Ian K. Y. Lo, Calgary (CA)

(73) Assignee: Soteria Industries, Inc., Calgary (CA)

( * ) Notice: Subject to any disclaimer, the term of this patent is extended or adjusted under 35 U.S.C. 154(b) by 658 days.

(21) Appl. No.: 14/459,435

(22) Filed: Aug. 14, 2014

(65) Prior Publication Data

US 2015/0047653 A1 Feb. 19, 2015

Related U.S. Application Data

(60) Provisional application No. 61/865,670, filed on Aug. 14, 2013.

(51) Int. Cl.
*A61F 5/37* (2006.01)

(52) U.S. Cl.
CPC .................. *A61F 5/3753* (2013.01)

(58) Field of Classification Search
CPC .................................................. A61F 5/3753
See application file for complete search history.

(56) References Cited

U.S. PATENT DOCUMENTS

| 5,665,058 A | 9/1997 | Young |
| 8,016,780 B1 | 9/2011 | Sickles |

| 2005/0273026 A1* | 12/2005 | Howard | A61F 5/3753 602/20 |
| 2011/0155148 A1* | 6/2011 | Golden | A61F 5/05841 128/878 |
| 2016/0022468 A1* | 1/2016 | Lo | A61F 5/373 602/20 |

FOREIGN PATENT DOCUMENTS

| WO | WO 03071994 A2 * | 9/2003 | .......... A61F 5/3753 |
| WO | WO-2011063155 A1 | 5/2011 | |

OTHER PUBLICATIONS

Extended European Search Report issued by the European Patent Office, dated Feb. 21, 2017, in corresponding European Patent Application No. 14842466.6.

* cited by examiner

*Primary Examiner* — Tarla Patel
(74) *Attorney, Agent, or Firm* — Locke Lord LLP; Daniel J. Fiorello; Bryan D. Zerhusen (57) ABSTRACT

The present disclosure provides exemplary arm immobilization devices for a person and associated methods of use. Thus, in one aspect, the disclosure provides a device including or comprising an outer shell including an internal cavity and a configurable structure disposed within the internal cavity of the outer shell. The outer shell can be configured and dimensioned to accommodate an arm of a person thereon. Expansion or contraction of the configurable structure can drive expansion or contraction of the outer shell. In another aspect, the disclosure provides methods for immobilizing an arm of a person that include providing an arm immobilization device and supporting the arm of the person with the outer shell and the configurable structure.

12 Claims, 11 Drawing Sheets

ARM IMMOBILIZATION DEVICE AND ASSOCIATED METHODS

CROSS-REFERENCE TO RELATED APPLICATIONS

This patent application claims priority to U.S. Provisional Application Ser. No. 61/865,670, filed on Aug. 14, 2013, titled "Arm Immobilization Device and Associated Methods", and is hereby expressly incorporated by reference as part of the present disclosure.

TECHNICAL FIELD

The present disclosure relates to arm immobilization devices and associated methods and, in particular, to universal arm immobilization devices which provide adjustable support to an arm of a person.

BACKGROUND

Various devices, such as shoulder slings, have been used in the medical industry to support an arm of a person after an injury, illness, surgery or during rehabilitation. Due to the variety of diverse applications for arm supports, immobilization devices have been designed for various conditions. However, different diagnoses commonly require different immobilization positions of the arm. For example, following an anterior shoulder dislocation, the arm may be immobilized in a sling with the arm positioned in adduction and internal rotation. In contrast, following a posterior shoulder dislocation, the arm may be immobilized in a sling with the arm positioned in a slight abduction and external rotation.

Figure 1:
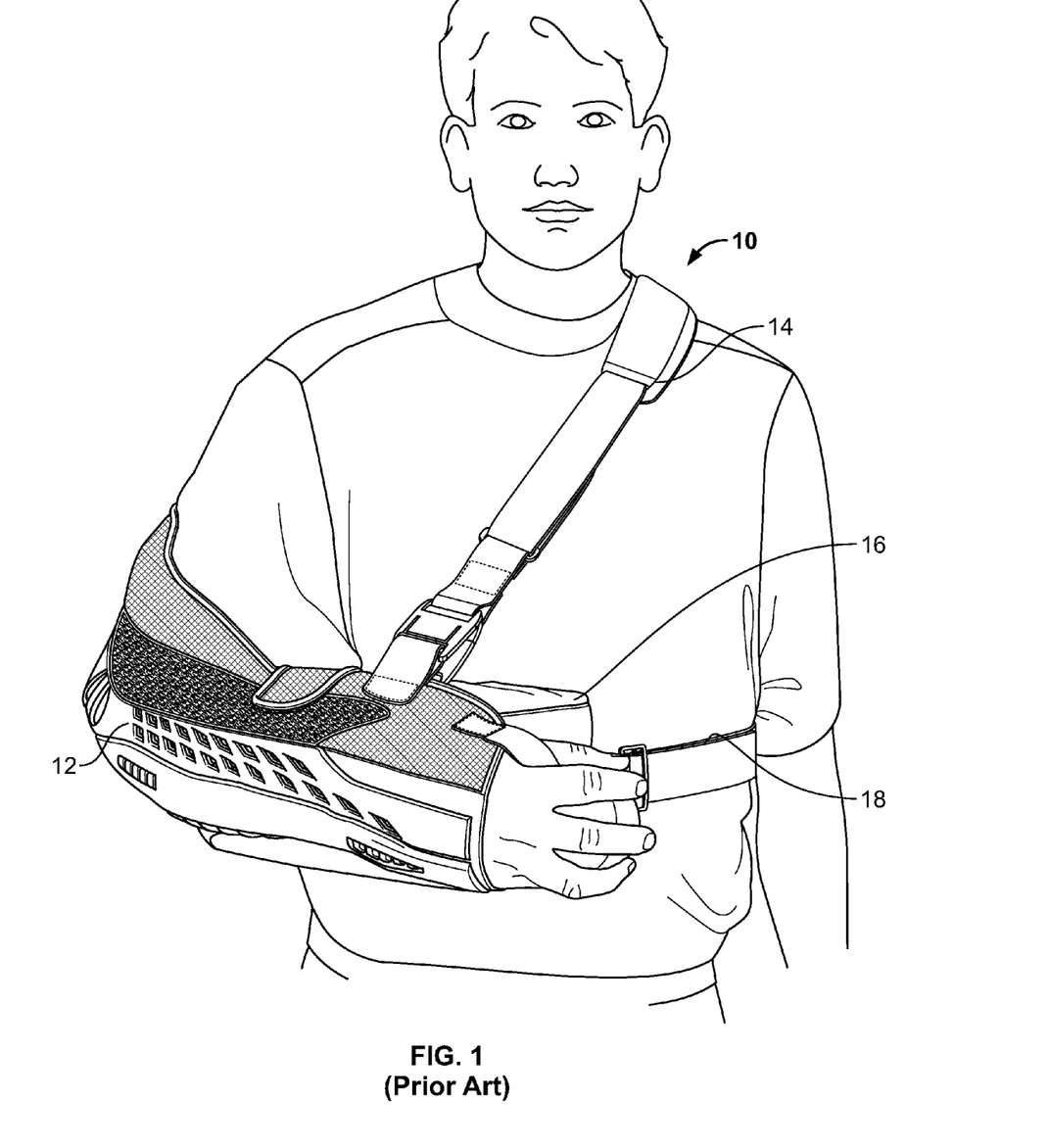
FIG. 1 shows a front view of a traditional arm immobilization device of the prior art.

FIG. 1 shows a traditional arm immobilization device 10, e.g., a sling, which generally includes a sleeve or pouch 12 for receiving the forearm and/or elbow and a shoulder and/or neck strap 14 which fits around the shoulder or neck of the person to support the weight of the arm. Some arm immobilization devices 10 can include a pouch 12 and strap 14 in combination with a side bolster 16 and side strap 18 to provide additional support to the arm, e.g., a DonJoy ULTRASLING®. However, the shoulder and/or neck straps of slings generally create a substantial amount of pressure on the shoulder or neck due to the weight of the arm being supported.

Figure 2:
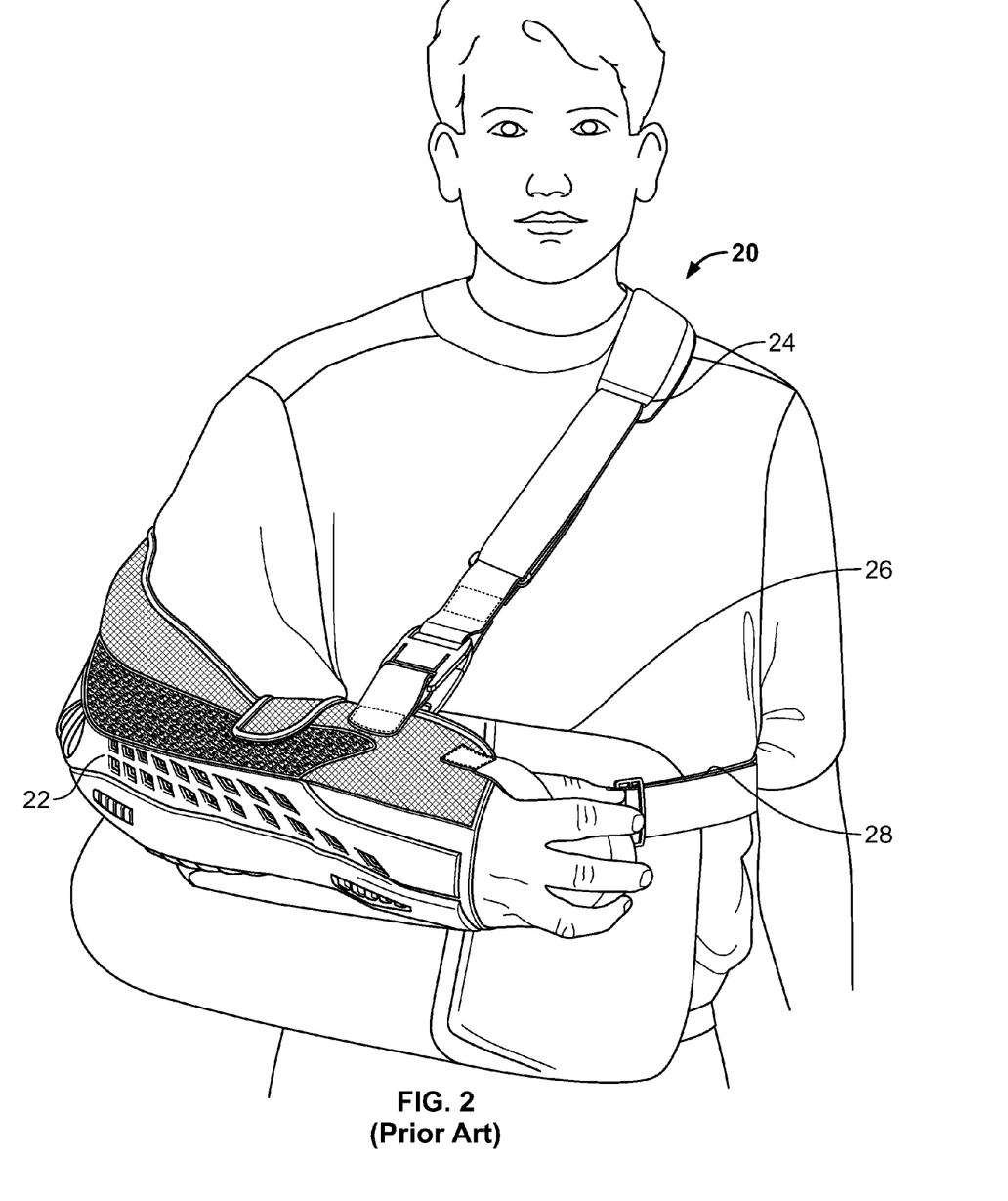
FIG. 2 shows a front view of a traditional arm immobilization device of the prior art.

FIG. 2 shows an alternative traditional arm immobilization device 20, e.g., a sling, which generally includes a sleeve or pouch 22 for receiving the forearm and/or elbow and a shoulder and/or neck strap 24. Some arm immobilization devices 20 can include a side bolster 26 and a side strap 28 which allow positioning of the arm in various angles depending on the shape of the bolster 26, e.g., a DonJoy ULTRASLING® III. For example, the device 20 of FIG. 2 may be implemented to position the arm at approximately 15 degrees of abduction and approximately 30 degrees of internal rotation. As shown in FIG. 2, the arm is positioned in abduction.

Figure 3:
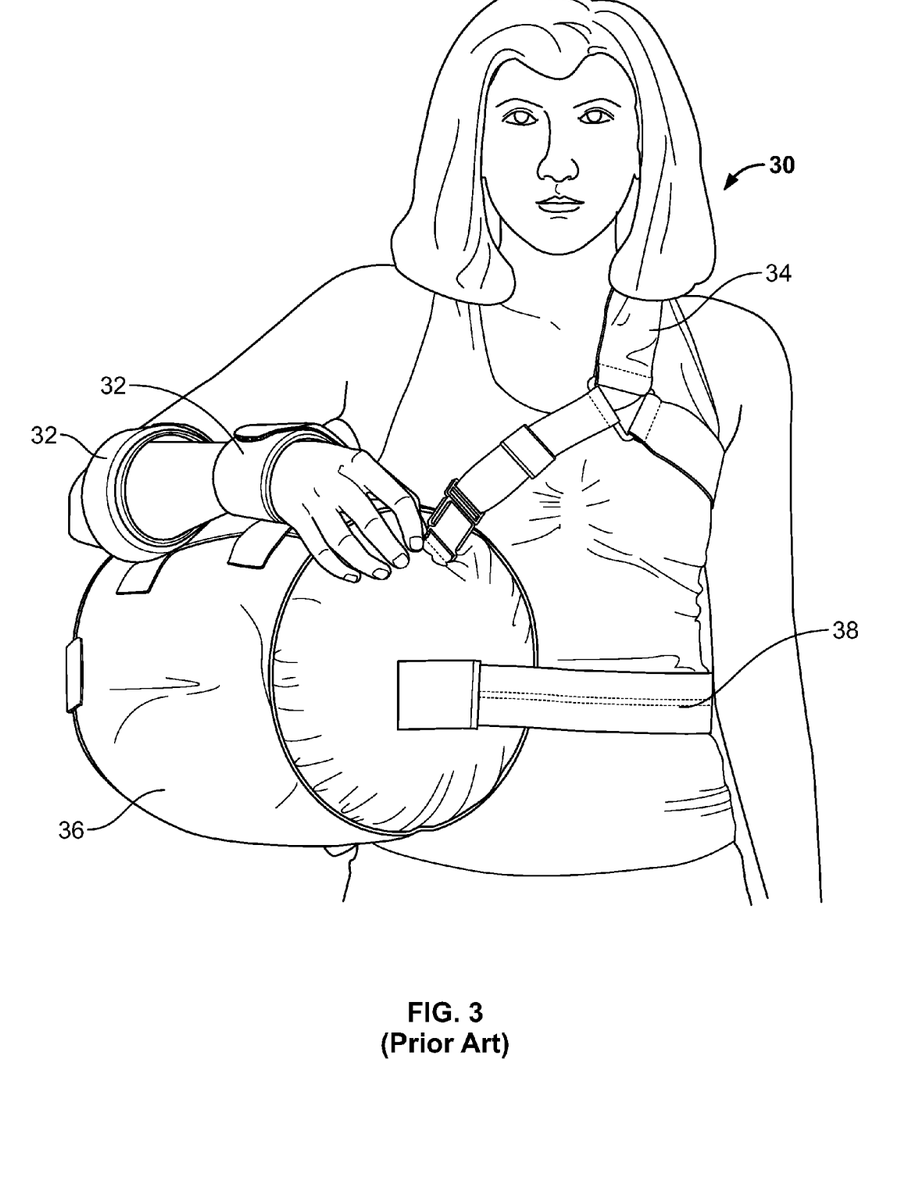
FIG. 3 shows a front view of a traditional arm immobilization device of the prior art.

Similarly, FIG. 3 shows an alternative traditional arm immobilization device 30 which generally includes arm straps 32, a shoulder and/or neck strap 34, a bolster 36 and a side strap 38. The arm straps 32 can be fastened around the arm and can be further secured to the bolster 36 to position in arm in various angles around the bolster 36.

Figure 4:
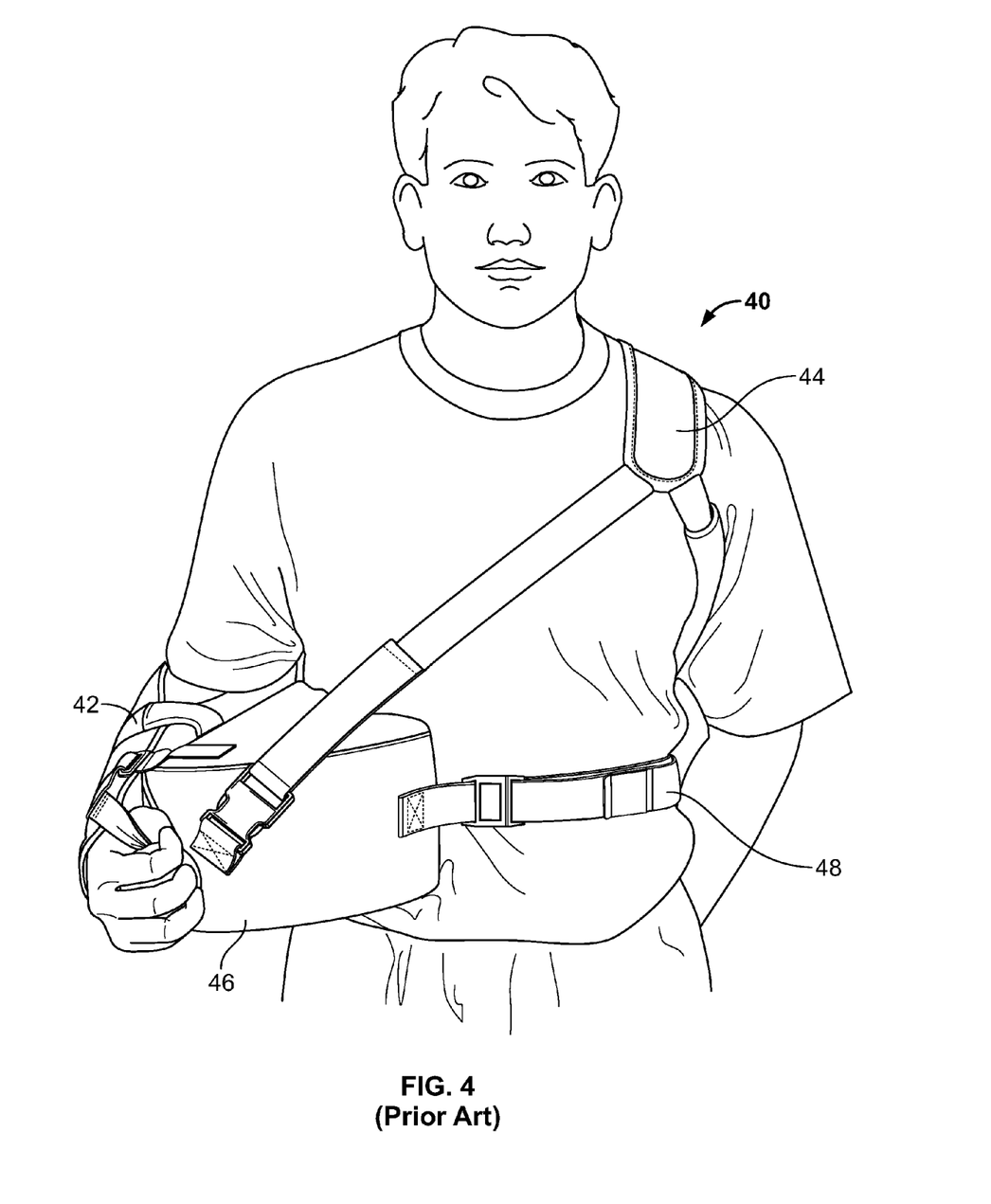
FIG. 4 shows a front view of a traditional arm immobilization device of the prior art.
Figure 5:
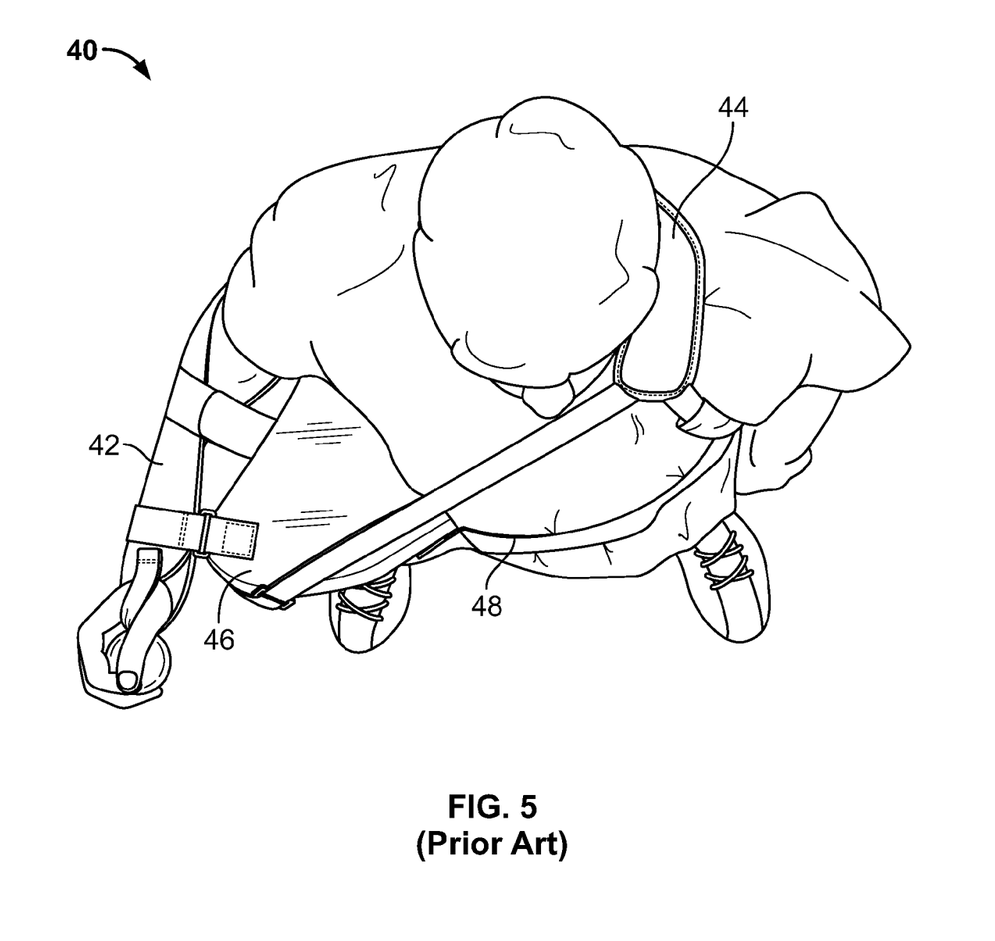
FIG. 5 shows a top view of a traditional arm immobilization device of the prior art.
Figure 6:
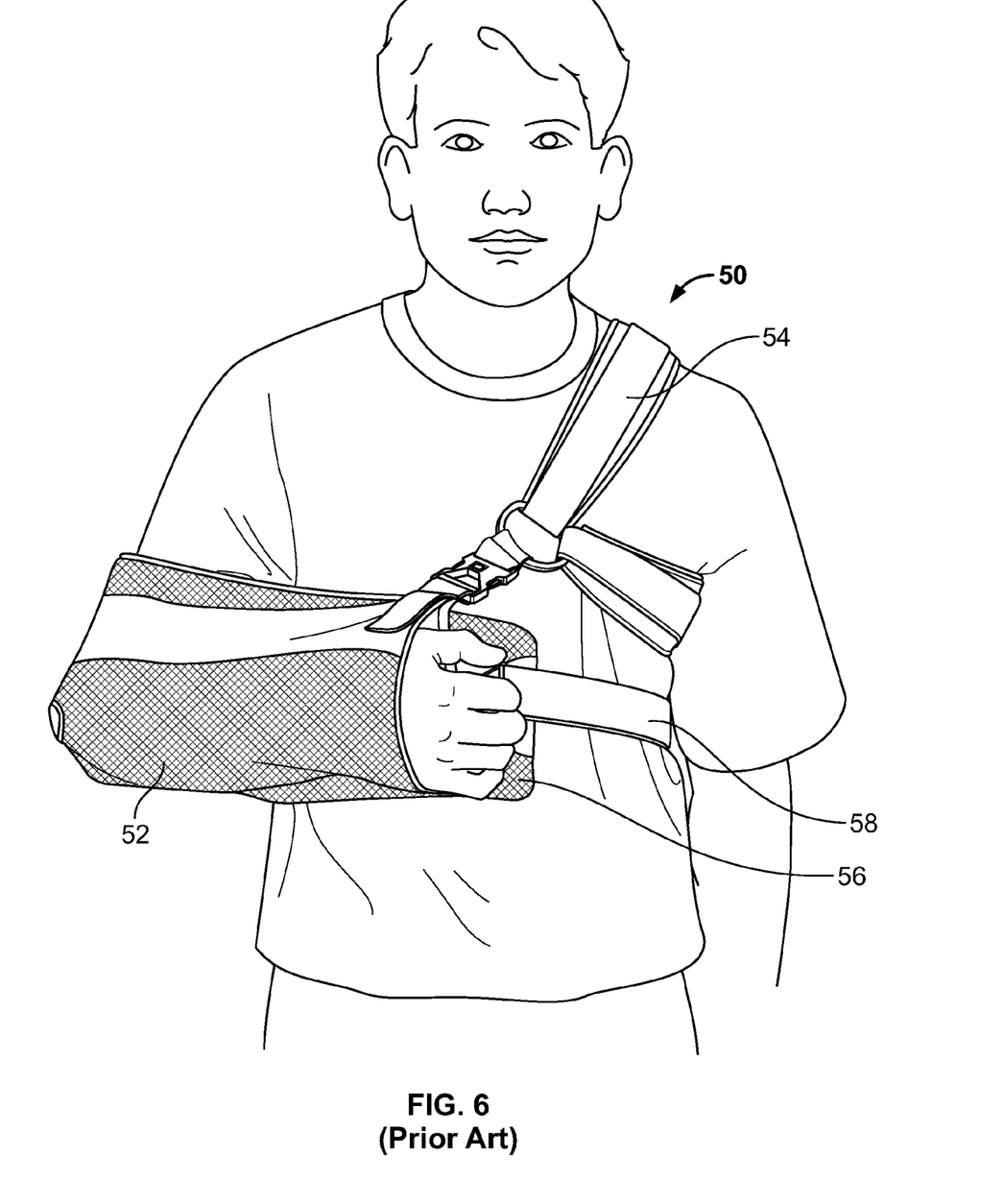
FIG. 6 shows a front view of a traditional arm immobilization device of the prior art.

FIGS. 4 and 5 show front and top views of an alternative traditional arm immobilization device 40 which generally includes a sleeve or pouch 42, a shoulder and/or neck strap 44, a bolster 46 and a side strap 48. The device 40 of FIGS. 4 and 5 may be implemented to position the arm at predetermined degrees of external and internal rotation. For example, FIGS. 4 and 5 show the arm secured in an external rotation position. However, the traditional arm immobilization devices of FIGS. 1-5 can typically only place the arm in a single position with no ability to adjust abduction, adduction, internal rotation and/or external rotation positioning. In addition, these devices typically do not provide precise immobilization of the injured or recovering arm and/or shoulder and can be challenging with respect to adjusting the positioning of the arm.

Figures 7A, 7B, 7C:
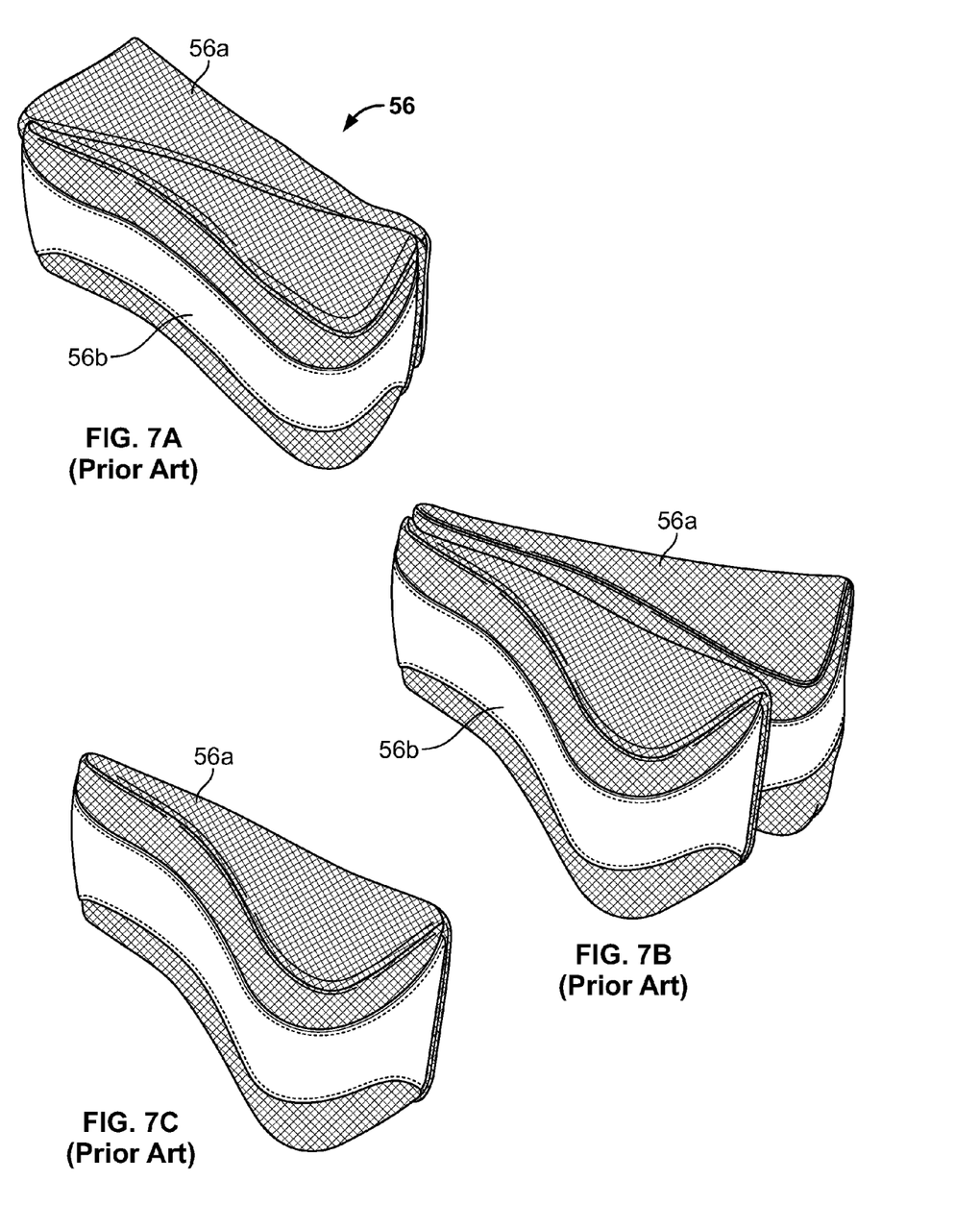
FIGS. 7A-7C show perspective views of traditional modifiable bolsters for an arm immobilization device of the prior art.

FIGS. 6 and 7A-7C show an alternative traditional arm immobilization device 50 which generally includes a sleeve or pouch 52, a shoulder and/or neck strap 54, a bolster 56 and a side strap 58. The bolster 56 can be a modifiable bolster 56, allowing the arm to be placed in different positions of internal rotation, a neutral position or external rotation, e.g., a Breg SLINGSHOT®3. The modifiable bolster 56 can be constructed from two parts or wedges, e.g., a first wedge 56a and a second wedge 56b, which, when constructed in the different configurations shown in FIGS. 7A-7C, allow different positions of the arm to be obtained. For example, FIG. 7A shows the bolster 56 configured for a neutral position of the arm, FIG. 7B shows the bolster 56 configured for an external rotation position of the arm, and FIG. 7C shows the bolster 56 configured for an internal rotation of the arm. However, the modifiable positions are generally fixed to only three different positions of the bolster 56 and provide no adjustability in abduction.

Figure 8:
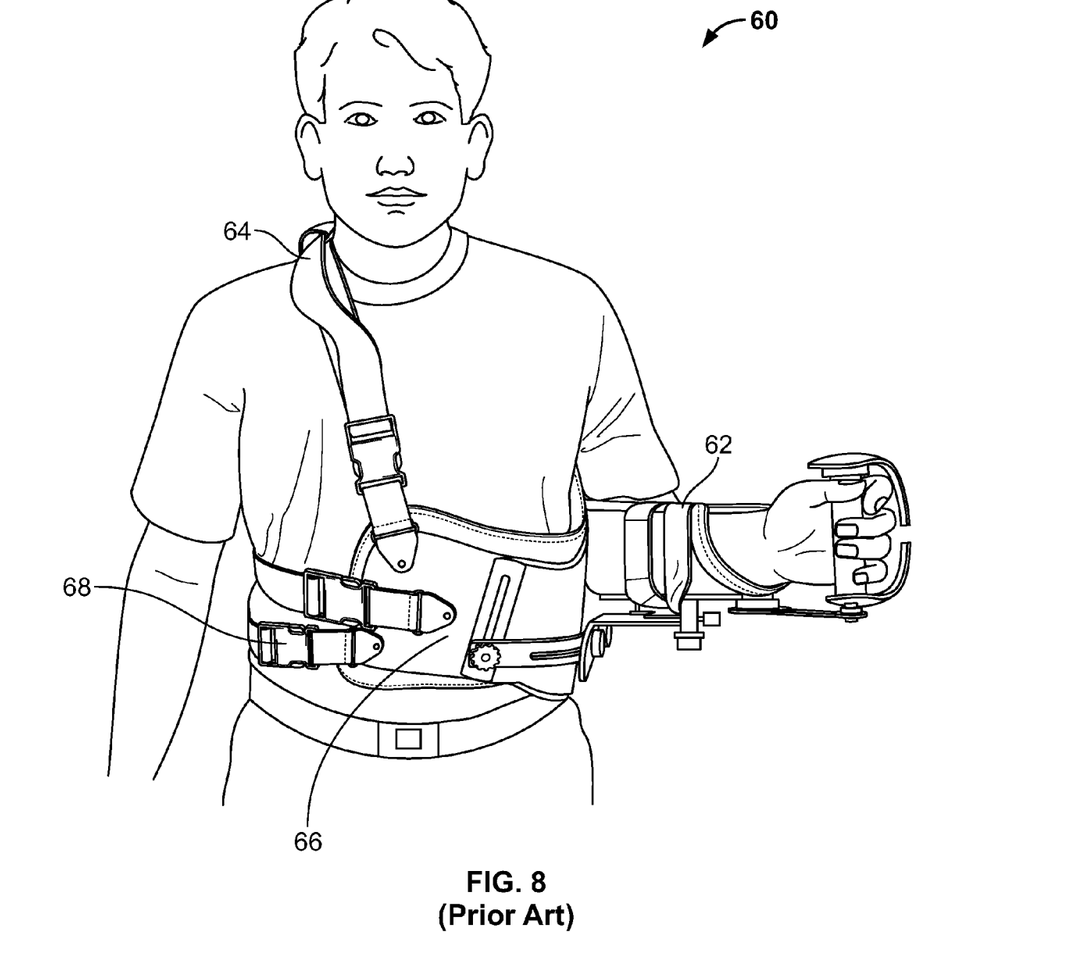
FIG. 8 shows a front view of a traditional arm immobilization device of the prior art.

FIG. 8 shows an alternative traditional arm immobilization device 60 which generally includes an arm support 62, a shoulder and/or neck strap 64, a thorax brace 66 and side straps 68. The device 60 of FIG. 8 generally requires a substantial amount of thorax bracing and/or metal components to provide the desired support to the arm, thereby complicating adjustment of the degree of internal or external rotation of the arm.

Thus, a need exists for arm immobilization devices and associated methods which substantially reduce the pressure to the shoulder, neck and/or upper torso of the person and provide convenient means for adjusting the position of the arm being supported. These and other needs are addressed by the devices and methods of the present disclosure.

SUMMARY

The present disclosure provides exemplary arm immobilization devices for a person and associated methods of use. Thus, in one aspect, the disclosure provides a device including or comprising an outer shell including an internal cavity. In certain embodiments, the arm immobilization device also includes a configurable structure disposed within the internal cavity of the outer shell. In an exemplary embodiment, the outer shell is configured and dimensioned to accommodate an arm of a person thereon. In additional embodiments, expansion or contraction of the configurable structure drives expansion or contraction of the outer shell.

In another exemplary embodiment, the arm immobilization device, as described herein, comprises two outer shells including a configurable structure in the internal cavity. In certain embodiments, at least one of the outer shells is configured and dimensioned to accommodate a detachable brace as described herein.

In any of the embodiments described herein, the outer shell and/or the configurable structure can be utilized to at least provide support from below for the arm of the person.

In any of the embodiments described herein, the device includes one or more of a shoulder strap, neck strap, or side strap.

In certain embodiments, the outer shell can include or comprise a fastener, e.g., VELCRO®, one or more buttons, and the like, thereon for detachably securing the outer shell to a belt secured around a torso of the person. In additional embodiments, a position of the outer shell relative to the belt can be adjustable along a circumference of the belt and/or a vertical direction along the belt. In further embodiments, the outer shell and the configurable structure can provide support to the arm of the person.

In certain embodiments, the outer shell can be configured and dimensioned to accommodate a detachable brace thereon. In further embodiments, the outer shell can define an accordion structure. The outer shell can include or comprise planar side surfaces, while the remaining surfaces define the accordion structure. In additional embodiments, the configurable structure can be at least one of, e.g., an air-filled bladder, a liquid-filled bladder, one or more springs, a spring mechanism, a squeezable foam, a memory foam, and the like. In certain embodiments, the device includes or comprises one or more adjustable straps for regulating a direction of expansion or contraction of the configurable structure. The one or more adjustable straps can include a buckle or a ratchet mechanism. Expansion or contraction of the configurable structure can be adjustable for varying degrees of at least one of, e.g., abduction, adduction, internal rotation, external rotation, combinations thereof, and the like.

In an additional aspect, the present disclosure provides exemplary methods for immobilizing an arm of a person that include providing an arm immobilization device as described herein. In certain embodiments, the exemplary methods include the step of supporting the arm of the person with the outer shell and the configurable structure.

In additional embodiments, the exemplary methods include detachably securing the outer shell to a belt secured around a torso of the person and adjusting a position of the outer shell relative to the belt along a circumference of the belt and a vertical direction along the belt. In certain embodiments, the exemplary methods include securing the arm of the person to the outer shell. In further embodiments, the exemplary methods include expanding or contracting the configurable structure to drive expansion or contraction of the outer shell.

In additional embodiments, the exemplary methods include adjusting expansion or contraction of the configurable structure to vary a degree of at least one of abduction, adduction, internal rotation, external rotation, combinations thereof, and the like. In certain embodiments, the exemplary methods include regulating a direction of expansion or contraction of the configurable structure by adjusting a length of adjustable straps secured to the outer shell. The adjustable straps can control expansion or contraction of the outer shell.

Other objects and features will become apparent from the following detailed description considered in conjunction with the accompanying drawings. It is to be understood, however, that the drawings are designed as an illustration only and not as a definition of the limits of the invention.

BRIEF DESCRIPTION OF THE DRAWINGS

To assist those of skill in the art in making and using the disclosed devices and associated methods, reference is made to the accompanying figures, wherein.

DESCRIPTION OF EXEMPLARY EMBODIMENTS

Figure 9:
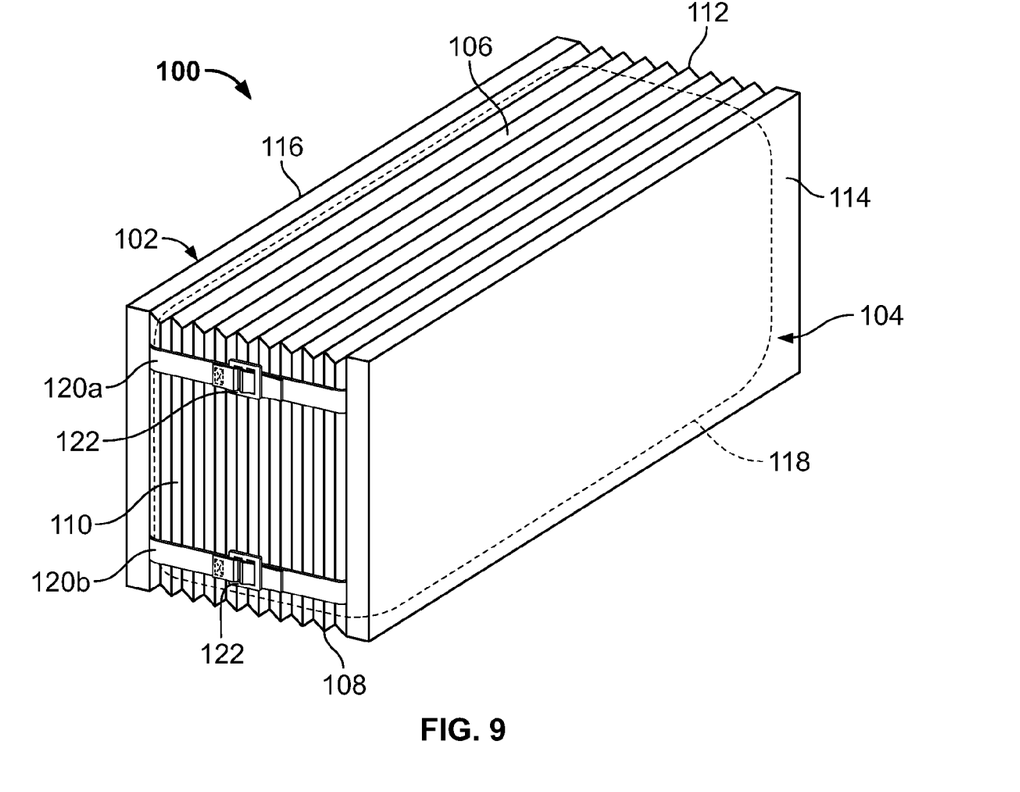
FIG. 9 shows a front perspective and cross-sectional view of an exemplary arm immobilization device.

With reference to FIG. 9, a front perspective view of an exemplary arm immobilization device 100 (hereinafter "device 100") is provided. The device 100 can be a universal or multi-adjustable arm immobilization, bolster or sling device 100 which provides multiple adjustment for patient-specific and/or diagnosis-specific immobilization of the arm. The device 100 further allows variable adjustment for internal rotation, external rotation, abduction and/or adduction of the arm. Thus, for example, the modular device 100 can be configured in a desired position of the arm immediately after surgery and the configuration can be varied or adjusted by the patient or doctor post-operation during rehabilitation.

The exemplary device 100, e.g., a bolster, can be implemented with a pouch, sleeve or brace (not shown) which at least partially receives the arm of a person. For example, the pouch, sleeve or brace can receive the arm of a person and straps, such as VELCRO® straps, can be used to secure the arm within the pouch or sleeve. The device 100 can include an outer shell 102 which forms an internal cavity 104 therein. The outer shell 102, e.g., a sleeve, can define a modifiable, adjustable or flexible structure. In some embodiments, the outer shell 102 can be fabricated from, e.g., plastic, vinyl, cloth, combinations thereof, and the like. In some embodiments, the outer shell 102 can define an accordion style structure on the top surface 106, the bottom surface 108, the front surface 110 and the back or rear surface 112, while defining a planar surface on the proximal and distal side surfaces 114, 116. Thus, the top, bottom, front and rear surfaces 106, 108, 110, 112 can be expanded or contracted in four directions substantially independently relative to each other for adjustment of the configuration of the outer shell 102. The flexible outer shell 102 allows multiple angles of adjustment in the two planes of abduction and adduction and internal and external rotation. The device 100 therefore combines the functionality of multiple shoulder or arm braces into one adjustable bolster, thereby reducing inventory.

The outer shell 102 can be configured and dimensioned to support the pouch, sleeve or brace thereon. In some embodiments, the proximal and/or distal side surfaces 114, 116 can include VELCRO® fasteners or buttons thereon for securing the device 100 to complementary VELCRO® or buttons on a belt (not shown) worn around the waist or torso of a person. The device 100 can be reversible, i.e., the device 100 can be attached with the proximal or distal side surface 114, 116 to the belt for support of the right arm and can be flipped or turned and attached to the belt with the proximal or distal side surface 114, 116 to support the left arm. In some embodiments, the proximal and distal side surfaces 114, 116 can be formed from a stiffer material, e.g., a stiff foam material, than the top, bottom, front and rear surfaces 106, 108, 110, 112. In some embodiments, the top and bottom surfaces 106, 108 can include VELCRO® thereon for securing the pouch, sleeve or brace. For example, the pouch, sleeve or brace can include complementary VELCRO® on a bottom or side surface such that the pouch, sleeve or brace can be positioned and secured along the top or bottom surface 106, 108 of the device 100.

The device 100 generally includes an internal configurable structure 118 disposed within the cavity 104 of the outer shell 102 to support expansion and contraction of the outer shell 102. In some embodiments, the configurable structure 118 can be, e.g., an air-filled bladder, a liquid-filled bladder, one or more springs, one or more spring-like mechanisms, memory foam, squeezable foam, combinations thereof, and the like, enclosed by the outer shell 102. In some embodiments, the configurable structure 118 can be fabricated from, e.g., rubber, elastic vinyl, plastic, combinations thereof, and the like. The outer shell 102 can include an opening (not shown) which can be sealed and unsealed to provide access to the cavity 104 and the internal configurable structure 118.

In embodiments implementing an internal air-filled bladder fabricated from an elastic material, inflation and deflation of the air-filled bladder can be used to regulate opening/expansion and closing/contraction of the outer shell 102, respectively. Therefore, inflating or deflating the internal air-filled bladder drives expansion or contraction of the superior-inferior and anterior-posterior surfaces of the outer shell 102 of the device 100. Inflation or deflation of the air-filled bladder may be regulated through an inlet valve which can be opened or closed to maintain the desired pressure within the air-filled bladder.

Although illustrated as an oval bladder in FIG. 9, it should be understood that alternative bladder configurations can be used to ensure expansion or contraction of the bladder within all surfaces and/or corners of the cavity 104 of the outer shell 102. In embodiments implementing internal spring(s) or memory foam, expansion and contraction of the spring(s) or memory foam can be regulated to create the desired configuration of the outer shell 102. The internal configurable structure 118 thereby provides support for expansion or contraction of the outer shell 102 and provides an internal modifiable stiffness for supporting an arm of the person on the outer shell 102.

The device 100 can include two or more buckle belts or straps, i.e., a top buckle strap 120a and a bottom buckle strap 120b with a buckle 122, connected at four corners on each of the front and rear surfaces 110, 112. The top buckle strap 120a can be positioned adjacent to or spaced from the top surface 106 and the bottom buckle strap 120b can be positioned adjacent to or spaced from the bottom surface 108. The top and bottom buckle straps 120a, 120b can be implemented to control and limit the amount of expansion or contraction of each of the walls of the outer shell 102 when the internal configurable structure 118 is expanded or contracted. A length of each of the top and bottom buckle straps 120a, 120b can be individually adjustable to accurately and independently limit the amount of expansion or contraction of the walls of the outer shell 102, thereby limiting the area to which the configurable structure 118 can be expanded. Although illustrated on the front and rear surfaces 110, 112, in some embodiments, the buckle straps can be positioned on any of the surfaces of the device 100, e.g., superior, inferior, anterior and/or posterior surfaces, to help limit expansion of the outer shell 102. In some embodiments, rather than or in combination with the buckle straps, any means for limiting or enhancing contraction or expansion of the device 100 can be used, e.g., one or more ratchet mechanisms, one or more strings or ties, and the like.

For example, as will be discussed in greater detail below, the top buckle strap 120a on the front surface 110 can be tightened to contract the corner between the top surface 106 and the front surface 110. The bottom buckle strap 120b on the front surface 110 can be tightened to contract the corner between the bottom surface 108 and the front surface 110. Both the top and bottom buckle straps 120a, 120b on the front surface 110 can be tightened to contract the front surface 110. Similarly, the top buckle strap 120a on the rear surface 112 can be tightened to contract the corner between the top surface 106 and the rear surface 112. The bottom buckle strap 120b on the rear surface 112 can be tightened to contract the corner between the bottom surface 108 and the rear surface 112. Both the top and bottom buckle straps 120a, 120b on the rear surface 112 can be tightened to contract the rear surface 112. In some embodiments, the top buckle straps 120a on the front and rear surfaces 110, 112 can be tightened to contract the top surface 106. Similarly, the bottom buckle straps 120b on the rear and front surfaces 110, 112 can be tightened to contract the bottom surface 108. Therefore, by using a combination of expansion and contraction of the internal configurable structure 118, e.g., inflation and deflation of the internal air-filled bladder, and adjusting the lengths of the buckle straps, varying degrees of abduction, adduction, internal rotation and/or external rotation can be obtained.

Figure 10A:
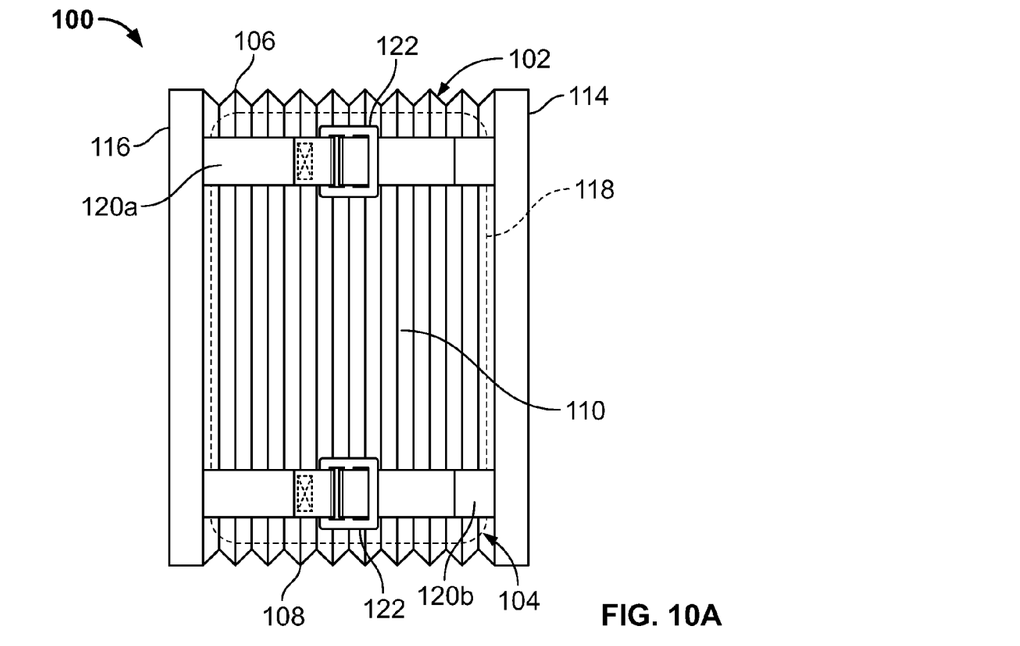
FIGS. 10A and 10B show side cross-sectional views of an exemplary arm immobilization device in configured for adduction and abduction.
Figure 10B:
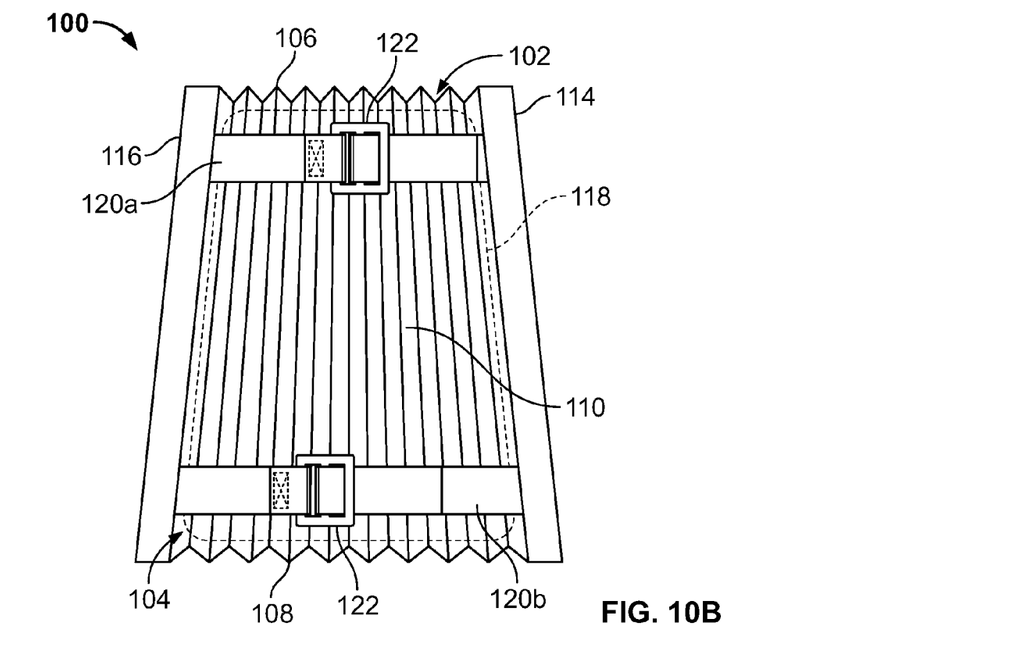

With reference to FIGS. 10A and 10B, side cross-sectional views of an exemplary device 100 are provided in adduction and abduction configurations. When viewed from above, abduction and adduction relate to the side-to-side positioning of an arm relative to the device 100 along the top surface 106. With respect to FIG. 10A, by contracting the internal configurable structure 118, e.g., deflating an air-filled bladder, and shortening the length of the top and bottom buckle straps 120a, 120b on the front and rear surfaces 110, 112, a narrow device 100 or bolster can be obtained to position the arm in relative adduction, i.e., positioning the arm closer to the torso of the person. With respect to FIG. 10B, by expanding the internal configurable structure 118, e.g., inflating the air-filled bladder, and loosening the lower or bottom buckle straps 120b on the front and rear surfaces 110, 112, the arm can be positioned in relative abduction, i.e., positioning the arm away from the torso of the person. Thus, adduction and abduction of the arm of the person can be adjusted as desired.

Figure 11A:
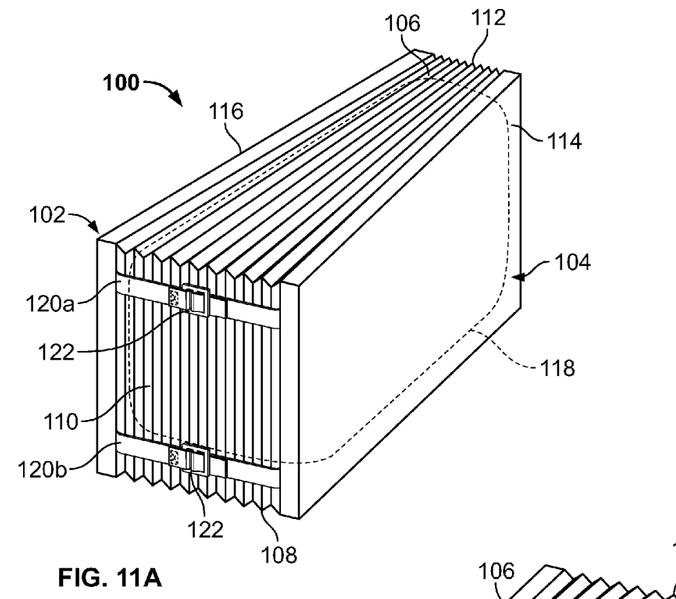
FIGS. 11A and 11B show front perspective and cross-sectional views of an exemplary arm immobilization device configured for external rotation and internal rotation.
Figure 11B:
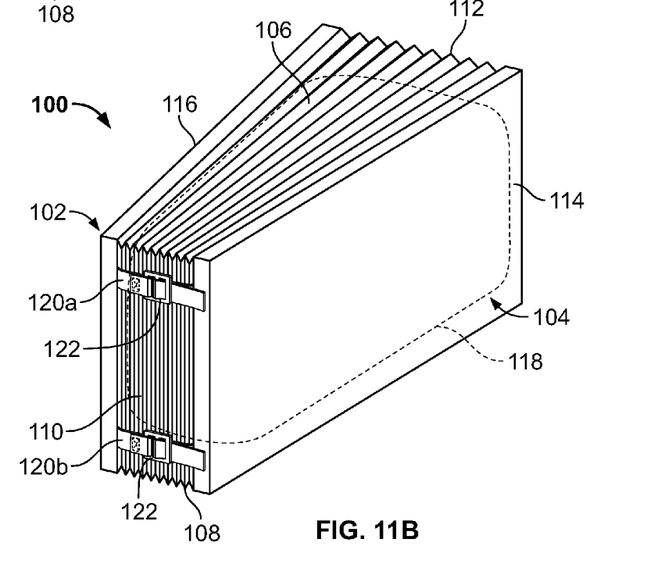

With reference to FIGS. 11A and 11B, front perspective and cross-sectional views of an exemplary device 100 are provided in external and internal rotation configurations. When viewed from above, internal and external rotation relate to the clockwise and counterclockwise rotation of the arm relative to the device 100 on the top surface 106. With reference to FIG. 11A, by expanding the internal configurable structure 118, e.g., inflating the air-filled bladder, shortening the length of the posterior top and bottom buckle straps 120a, 120b on the rear surface 112, and increasing the length of the anterior top and bottom buckle straps 120a, 120b on the front surface 110, a configuration or position of relative external rotation can be obtained, i.e., rotating the arm such that top surface 106 closest to the rear surface 112 which supports the elbow of the person is rotated closer to the torso of the person. With reference to FIG. 11B, by expanding the internal configurable structure 118, e.g., inflating the air-filled bladder, increasing the length of the posterior top and bottom buckle straps 120a, 120b on the rear surface 112, and shortening the length of the anterior top and bottom buckle straps 120a, 120b on the front surface 110, a configuration or position of relative internal rotation can be obtained, i.e., rotating the arm such that the top surface 106 closest to the rear surface 112 which supports the elbow of the person is rotated away from the torso of the person. Thus, rotational positioning of the arm of the person can be adjusted as desired.

Although illustrated in FIGS. 10A-11B in specific configurations, it should be understood that by using a combination of the techniques described above, any combination of adduction-abduction and/or internal-external rotation can be obtained through a limitless number of angles. In addition, the arm can be positioned near the front surface 110 or the rear surface 112 for flexion or extension of the arm. Thus, the device 100 allows the arm to be positioned in a desired and adjustable position following injury or surgery. For example, following a posterior dislocation, it may be desired to position the arm in slight abduction and external rotation. The device 100 can therefore be configured by expanding the internal configurable structure 118, e.g., inflating the air-filled bladder, tightening the posterior top and bottom buckle straps 120a, 120b on the rear surface 112, and loosening the anterior top and bottom buckle straps 120a, 120b on the front surface 110 to position the arm in slight abduction and external rotation.

As a further example, following an anterior dislocation, it may be desired to position the arm in adduction and internal rotation. The device 100 can therefore be configured by contracting the internal configurable structure 118, e.g., deflating the air-filled bladder, tightening the anterior top and bottom buckle straps 120a, 120b on the front surface 110, and loosening the posterior top and bottom buckle straps 120a, 120b on the rear surface 112 to position the arm in adduction and internal rotation.

The device 100 can also be used for patient specific post-operative immobilization. For example, during shoulder surgery, e.g., a total shoulder replacement, shoulder instability, and the like, the arm is commonly examined to determine where the shoulder is most stable. The device 100 can then be configured and customized using a combination of the internal configurable structure 118 expansion or contraction and the top and bottom buckle straps 120a, 120b specifically for the individual patient following surgery to support the arm where the shoulder is most stable.

The device 100 can further be used for alternative surgeries, such as rotator cuff repair. For example, by expanding the internal configurable structure 118, e.g., inflating the air-filled bladder, and loosening the inferior top and bottom buckle straps 120a, 120b, the arm can be positioned in various degrees of abduction, e.g., approximately 60 degrees of abduction. By increasing the amount of abduction, tension can be decreased at the rotator cuff tendon repair site, which can improve healing of the patient.

In addition to the precise immediate post-surgical or post-injury arm positioning, the device 100 allows adjustments and alternations of the arm position throughout the immobilization process and the follow-up period. For example, during repair of a massive rotator cuff tear, the surgeon may elect to position the arm in an extreme amount of abduction, e.g., approximately 60 degrees of abduction, by using a combination of internal configurable structure 118 expansion and loosening of the bottom buckle straps 120b on the front and rear surfaces 110, 112. In general, this position can be maintained for approximately six to eight weeks post-operatively to decrease tension at the repair site and potentially improve healing. However, while optimal for tendon healing, arm immobilization in an extreme amount of abduction can be awkward to maintain for a patient. Thus, following the six to eight weeks of healing, when support for the arm is suddenly discontinued, an extreme amount of tension can be experienced at the repair site, potentially risking failure and further injury.

The device 100 therefore allows precise, minor adjustments to the position of the arm throughout the post-operative rehabilitation phase to ensure proper healing. For example, during the six to eight weeks of immobilization, the patient can slowly contract the internal configurable structure 118, e.g., deflate the air-filled bladder, and tighten the bottom buckle straps 120b on the front and rear surfaces 110, 112 to lower the arm by approximately 5 to 10 degrees each week. This procedure can slowly apply tension to the repair site at minimal weekly increments. By the end of the six to eight weeks of immobilization, the arm can be at the side of the body, thereby preventing sudden tension at the repair site when the device 100 is removed.

The procedure discussed above can be performed in a quick and simple manner by the patient without assistance from a doctor and without any external tools. The procedure may also be performed by a doctor during follow-up consultations with the patient to ensure the proper modifications are made to the support provided by the device 100. The device 100 can therefore be implemented to provide support to a patient post-surgery and can be customized over time to assist in healing of the repair site.

While exemplary embodiments have been described herein, it is expressly noted that these embodiments should not be construed as limiting, but rather that additions and modifications to what is expressly described herein also are included within the scope of the invention. Moreover, it is to be understood that the features of the various embodiments described herein are not mutually exclusive and can exist in various combinations and permutations, even if such combinations or permutations are not made express herein, without departing from the spirit and scope of the invention.

The invention claimed is:

1. An arm immobilization device, comprising:
   an outer shell including an internal cavity, wherein the outer shell defines an accordion structure, wherein the accordion structure includes bellow-type pleats,
   a configurable structure disposed within the internal cavity of the outer shell, wherein the outer shell is configured and dimensioned to accommodate an arm of a person thereon, and
   wherein expansion or contraction of the configurable structure drives expansion or contraction of the outer shell one or more adjustable straps for regulating a direction of expansion or contraction of the configurable structure and wherein expansion or contraction of the configurable structure is adjustable for varying degrees of at least one of abduction, adduction, internal rotation and external rotation.

2. The arm immobilization device of claim 1, wherein the outer shell and the configurable structure provide support to the arm of the person.

3. The arm immobilization device of claim 1, wherein the outer shell is configured and dimensioned to accommodate a detachable brace thereon.

4. The arm immobilization device of claim 1, wherein the outer shell comprises planar side surfaces.

5. The arm immobilization device of claim 1, wherein the configurable structure is at least one of an air-filled bladder, a liquid-filled bladder, one or more springs, a spring mechanism, a squeezable foam, and a memory foam.

6. The arm immobilization device of claim 1, wherein the one or more adjustable straps include a buckle or a ratchet mechanism.

7. A method for immobilizing an arm of a person, comprising:
providing an arm immobilization device, the arm immobilization device including:
an outer shell including an internal cavity, wherein the outer shell defines an accordion structure, wherein the accordion structure includes bellow-type pleats, a configurable structure disposed within the internal cavity of the outer shell, and
supporting the arm of the person with the outer shell and the configurable structure adjusting expansion or contraction of the configurable structure to vary a degree of at least one of adduction, internal rotation and external rotation; regulating a direction of expansion or contraction of the configurable structure by adjusting a length of adjustable straps secured to the outer shell.

8. The method of claim 7, comprising detachably securing the outer shell to a belt secured around a torso of the person.

9. The method of claim 8, comprising adjusting a position of the outer shell relative to the belt along a circumference of the belt and a vertical direction along the belt.

10. The method of claim 7, comprising securing the arm of the person to the outer shell.

11. The method of claim 7, comprising expanding or contracting the configurable structure to drive expansion or contraction of the outer shell.

12. The method of claim 7, wherein the adjustable straps control expansion or contraction of the outer shell.

* * * * *